United States Patent
Galiana et al.

[11] Patent Number: 5,942,954
[45] Date of Patent: Aug. 24, 1999

[54] APPARATUS AND METHOD FOR MEASURING VESTIBULAR OCULAR REFLEX FUNCTION

[75] Inventors: Henrietta L. Galiana, St. Lambert, Canada; Ian W. Hunter; Lynette A. Jones, both of Lincoln, Mass.; James Tangorra, Boston, Mass.

[73] Assignee: Massachusetts Institute of Technology, Cambridge, Mass.

[21] Appl. No.: 09/134,329

[22] Filed: Aug. 14, 1998

Related U.S. Application Data

[60] Provisional application No. 60/056,642, Aug. 22, 1997, and provisional application No. 60/061,220, Oct. 7, 1997.

[51] Int. Cl.[6] .......................................... A61B 3/14
[52] U.S. Cl. ......................... 331/209; 600/546; 600/558
[58] Field of Search ..................... 351/200, 205, 351/209; 435/7.21; 607/54; 600/546, 558

[56] References Cited

U.S. PATENT DOCUMENTS

| | | | |
|---|---|---|---|
| 4,667,676 | 5/1987 | Gyinta | 607/54 |
| 4,817,633 | 4/1989 | McStravick et al. | 128/782 |
| 5,004,683 | 4/1991 | Erichsen et al. | 435/7.21 |

FOREIGN PATENT DOCUMENTS

| | | |
|---|---|---|
| 2 276 467 | 9/1994 | United Kingdom . |
| WO 83/03341 | 10/1983 | WIPO . |

OTHER PUBLICATIONS

"Vorteq® High Frequency VOR Test Equipment", *Micromedical Technologies, Inc.*, www.micromedical.com/vorteq.html, Mar. 20, 1998.

*Primary Examiner*—George Manuel
*Attorney, Agent, or Firm*—Bromberg & Sunstein LLP

[57] ABSTRACT

An apparatus and method for analyzing visual and vestibular responses of a subject. One or more targets undergoing slow random motion are presented to the subject while the head of the subject is simultaneous perturbed with perturbations statistically uncorrelated with the random motion of the target. The response of the motion of the head of the subject and the motion of the subject's eyes is measured and the visual and vestibular system response dynamics are estimated based on the measured response.

22 Claims, 4 Drawing Sheets

APPARATUS AND METHOD FOR MEASURING VESTIBULAR OCULAR REFLEX FUNCTION

The present application claims priority from U.S. provisional application number 60/056,642, filed Aug. 22, 1997. and U.S. provisional application number 60/061,220, filed Oct. 7, 1997, both of which applications are herein incorporated by reference.

TECHNICAL FIELD

The present invention pertains to a method and apparatus for simultaneously perturbing the head of a subject and the position of visual or auditory targets while monitoring the vestibular and ocular responses by means of sensors worn on the head of the subject.

BACKGROUND OF THE INVENTION

Dizziness and nausea are the major complaints leading to consultations in medical clinics or emergency units. Though many systemic problems can be associated with these symptoms, the majority are caused by deficits in the peripheral vestibular apparatus, or its associated projections in the brainstem and cerebellum. Despite this high clinical profile, there has been little change in the testing protocols, and large, expensive, and necessarily stationary equipment in hospital environments are required under current protocols.

It is generally assumed that the vestibulo-ocular reflex (VOR), for example, can be probed simply by comparing responses in the dark to those in the light with room- or body-fixed targets. The differences are normally ascribed to the visual system. These approaches are not technically correct, since the visual and vestibular processes in the brain share common pathways. Hence, we are actually dealing with a two-input system at all times (whether targets are imagined or provided).

Modern vestibular tests applied in a hospital otolaryngology clinic include:
  bedside qualitative observations of spontaneous or elicited nystagmus (e.g. by head-shaking);
  caloric irrigation (hold or cold) of the ear canal to probe asymmetries between right and left systems; and
  passive whole body rotation of a patient with selected speeds and profile, again to probe symmetry, linearity, and their modulation by interactions with visual goals (e.g. VOR dark vs. light VOR suppression while viewing head-fixed target).

It is known that any head motion (linear or angular) will cause eye movements consisting of two mixed segments: slow-phases, where the eyes and head move in opposite directions, and fast-phases (saccades) which redirect the gaze before the eyes reach motor limits. The ensemble of slow and fast phases is referred to as ocular nystagmus. The usual measures of VOR function include the gain (eye velocity/head velocity) and phase of the slow-phase trajectories during sinusoidal rotations or linear motions. Because these tests are performed by rotating the subject's entire body, large high-torque motors are required—an expensive approach not readily applicable to home or community clinic use.

Classically, test protocols are based on the assumption that visual and vestibular systems can be assessed independently, and that VOR tests in the dark reflect the dynamics of the default system with no visual goals. In fact, dark responses can be modulated even by imagined targets and so can be very labile; furthermore, the visual and vestibular oculomotor system share most of the relevant pathways in the brainstem. As a result, the dynamics and linearity of apparent VOR responses will be sensitive to any correlation with real or imagined visual goals. This explains why the measured 'VOR' gain rises to one (perfect compensation) when viewing an earth fixed target, and drops to less than 0.3 when viewing a head-fixed target. The 'default' value in the dark can vary between 0.5–0.8 in normal adults, and one wonders what purpose a VOR in the dark can serve operationally, sine the ultimate goal is stabilization of a regtinal field, using both visual and vestibular sensors.

Often tests of the VOR in the dark cannot distinguish easily between normal subjects, and vestibular patients who have had time to adjust or compensate for their deficits. It is even more difficult to detect differences between those compensated patients leading normal lives, and those complaining of nausea or degradation of life style. These issues are important for separating malingerers from true patients, and for the certification of employees in high-risk jobs (e.g. airplane pilots, large vehicle controllers, high-rise construction workers, etc. It would be more appropriate to test subjects using a more normal context of visual and vestibular co-stimulation, since it is their performance when active and viewing targets, not in the dark or when their eyes are closed, that affects comfort level and functional limits.

The length of clinical rotation tests is another issue. Often, the dynamics are probed using single sinusoids, and varying amplitudes are applied to test linearity; hence such tests can be very time-consuming for a patient and have a high risk of subject malaise. Those few clinics which instead apply pseudo-random test sequences have the advantage of short test periods, but again rely on large motor platforms, and classical dark/light test conditions, which, as mentioned above, lead to correlated input conditions.

SUMMARY OF THE INVENTION

In accordance with a preferred embodiment of the invention, there is provided a method for analyzing visual and vestibular responses of a subject, the method having the steps of:

a. Displaying to the subject at least one target undergoing slow random motion;

b. perturbing the head of the subject with perturbations statistically uncorrelated with the random motion of the at least one target;

c. measuring at least one dimension of motion of the head of the subject;

d. measuring a dimension of motion of at least one eye of the subject; and e. estimating visual and vestibular system response dynamics based on the measured head and eye responses to dual perturbations.

In accordance with an alternate embodiment of the invention, the method may also compare the measured response of the subject with accumulated data in such a manner as to distinguish a functionally normal subject from a functionally deficient subject with identical stimuli. A method may be provided for analyzing the interaction between vergence, head processing, and conjugate eye reflexes in a subject by measuring the response of the motion of the head of the subject and the motion of two eyeballs of the subject, and a method may be provided for classifying the qualification of an individual for a specified function by comparing the measured response of the individual with predetermined ranges of acceptable responses in such a manner as to distinguish a capable candidate from a deficient candidate. A method may also be provided for rehabilitating a subject suffering from a vestibular deficiency, the method having the steps of determining the vestibular deficits of the subject, displaying to the subject at least one target undergoing slow random motion, perturbing the head of the subject with perturbations programmed to stimulate correction of the vestibular deficits of the subject.

In accordance with another aspect of the present invention, a portable apparatus is provided for analyzing visual and vestibular responses of a subject. The apparatus has a perturber for applying a torque perturbation to the head of the subject and a transducer for measuring the torque applied to the head of the subject. Additionally, the apparatus has a head position tracker for measuring rotational movement of the head of the subject, an eye tracker for measuring the motion of at least one eyeball of the subject, and a processor for estimating visual and vestibular system response dynamics based on the measured rotational movement of the head of the subject and motion of at least one eyeball of the subject. The apparatus may have several means for applying torque perturbations to the head such as a well-fitted helmet or headphone geometry. The perturbation mechanism can include fluid jets (air or water), a servomotor driving a reaction ring disposed circumferentially about the head attachment device (e.g., helmet or headphone) or a direct drive Lorentz force actuator driving a conductive liquid or solid metal ring circumferentially about the head attachment device. The head position tracker may be a rotational velocity sensor, and the eye tracker may be an electro-oculograph, or a corneal reflection eye tracker.

BRIEF DESCRIPTION OF THE DRAWINGS

The invention will more readily be understood by reference to the following description taken with the accompanying drawings, in which.

The drawings are intended to provide a better understanding of the present invention, but are in no way intended to limit the scope of the invention.

DETAILED DESCRIPTION OF SPECIFIC EMBODIMENTS

In accordance with preferred embodiments of the present invention, both visual and vestibular inputs are controlled during experimental testing, preferably providing statistically uncorrelated visual and vestibular goals to the subject. The system can perturb a subject's head during natural head-free turns, using 10% of normal peak torques (~1 N–m) while the subject either views slowly-moving random targets displayed in a visor or projected onto a distant screen, or follows three-dimensional acoustic targets presented through headphones. Such a portable helmet-mounted system advantageously allows less costly and fast simultaneous observations of a subject's visual and vestibular responses. The use of uncorrelated inputs provides consistent estimation of response dynamics from each system, despite potential internal interactions. The application of new linear and non-linear identification tools, together with algorithms to classify and sort response segments in nystagmus, will provide more powerful tools than currently known to distinguish functionally normal subjects, despite lesions, from subjects with true vestibular deficiencies. These tools may be applied advantageously not only for diagnosis and rehabilitation, but also for the certification of subjects in high-risk occupations (pilots, controllers of heavy equipment, high-rise construction workers, etc.).

Figure 1:
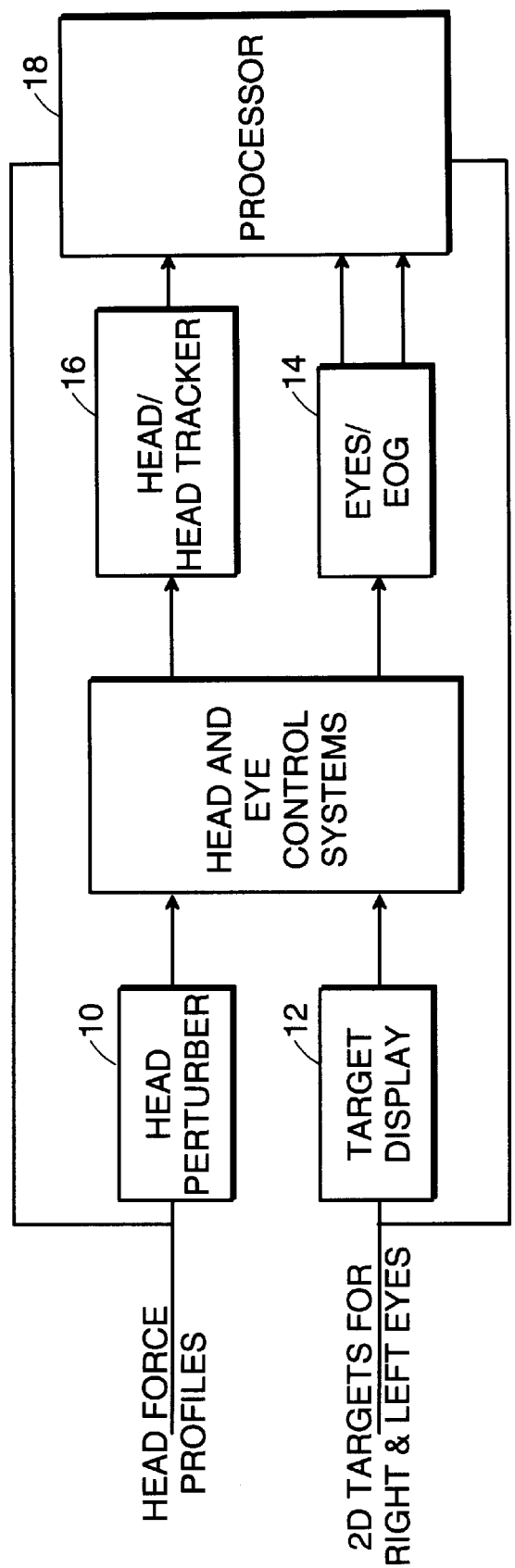
FIG. 1 depicts a schematic diagram of an apparatus for perturbing the head of a subject and monitoring vestibular and ocular response, in accordance with a preferred embodiment of the present invention.

Referring to FIG. 1, a preferred embodiment of the present invention is depicted schematically. In accordance with this embodiment, the head position of a subject is perturbed by Head Perturber 10 while randomized visual targets are presented to the subject, for example, by a Head's Up Display 12. The head perturbation and visual stimulation occur simultaneously, and head and binocular positions are simultaneously recorded. Analysis algorithms provide numeric models (parametric and non-parametric), including non-linear models, for the VOR in the dark, in the light, and for pursuit both eccentrically and in depth. The visual and vestibular stimuli are designed to have stochastically uncorrelated trajectories for optimal identification of the vestibular and visual tracking systems.

In accordance with preferred embodiments of the invention, experimental protocol designs provide for presentation to the subject of optimal stimuli and for recording head and binocular positions while the subject's head is free to assist target tracking.

Different methods are known in the art for perturbing the position of the head of the subject. By way of example, head perturber 10 may use jets of a fluid, such as water or air, controlled by a Coanda based switching valve, for torques up to at least 1 N–m. Since normal VOR responses are linear to 250°/s, the combination of active and perturbed trajectories preferably exceed this speed. Action axes are preferably arranged in two mirrored 3-D configurations, to provide up to 6-dimensional mutually orthogonal stochastic binary sequences of acceleration, with three dimensions each of angular and linear perturbations of the head. Heads-Up Display 12 preferably includes, by way of example, heads-up dual chromic display panels able to provide randomized retinal errors, the display panels being individually controlled for each eye, with up to ±40-degree retinal deviations.

Motion of the eyes of the subject is tracked by an Eye Tracker 14. Many technologies are known for tracking eye movements and are within the scope of the present invention as described and as claimed in any appended claims. In a preferred embodiment of the invention, eye tracking is performed using electro-oculographic (EOG) or non-contact video-based eye trackers to provide binocular 2D trajectories. A Head Tracker 16 tracks the motion of the head of the subject and may be magnetically-based (Polhemus or Ascension) or inertial-based (DC accelerometer or magnetohydrodynamic rotational velocity, for examples) tracker for providing a head rotation-translation matrix. The head tracking sensor should have a bandwidth exceeding 20 Hz.

Input data streams to Head Perturber 10 and Heads-Up Display 12 as well as signal outputs of Eye Tracker 14 and Head Tracker 16 are processed by processor 18 and recorded on PC-based hardware capable of at least 100 Hz rates. Analysis software running on processor 18 performs the following functions:

sorting responses into intervals corresponding to slow and fast phases (saccades);

grouping appropriate interval types for estimating transfer functions; and applying correlation or spectral analysis if gaze holding is normal or transient analysis if gaze holding decay is present.

Since ocular responses in any protocol contain nystagmus, the software package preferably includes automatic classification of eye (or gaze) slow and fast phases, based, for example, on classification software described by Rey & Galiana, "Parametric classification of segments in ocular nystagmus," *IEEE Trans. Biomed. Eng.*, vol. 38, (1991), pp. 142–48, which is incorporated herein by reference. A U.S. provisional patent application entitled "Automated Segmentation of Nystagmus or Other Complex Curves," and filed Feb. 18, 1998 is also incorporated herein by reference. Since the visual and head perturbing inputs are uncorrelated, visual and vestibular reflexes can be estimated without bias.

In the described approach, the subject's neck muscles are providing the major portion of the torque required to reach large head speeds. Thus, large DC motors for moving the whole body are not required. Perturbations are used to probe the systems about these operating points. A large range of head velocities (the determining factor in the linearity of the VOR) may be obtained by appropriate timing of large retinal errors. The natural coordination of eyes and head during gaze shifts cause larger and larger head speeds as target eccentricity on the retina increases, as discussed, for example, by Galiana & Guitton, "Central organization and modeling of eye-head coordination during orienting gaze shifts," in *Annals of the N.Y. Academy of Science*, vol. 656 (1992), pp. 452–71, which is herein incorporated by reference.

In the special case of visual targets presented at optical infinity, both eyes should respond identically to combined visual/vestibular stimulation. Any discrepancies in the responses of each eye flag an abnormality incompatible with the geometrical demands. Hence, it is useful to record simultaneously the head trajectory and binocular trajectories. This also permits the testing of interactions between the vergence system (targets moving in depth) and conjugate VOR responses; geometry requires that the VOR modulate on-line with target depth and eccentricity, since the eyes do not lie on the head's center of rotation, as discussed in Cova & Galiana, "A bilateral model integrating vergence and the VOR," *Experimental Brain Research*, vol. 107, (1996), pp. 435–452, which is incorporated herein by reference. Hence, the helmet approach, described below, may also be used to test linear motion sensors, and interactions with vergence control.

Analysis of data obtained by performing the method described above is now discussed with reference to FIGS. 2A and 2B. For the sake of simplifying the discussion, the example here is restricted to the horizontal system (rotation about a vertical axis through the head), however the analysis is readily extended to six dimensions (three rotational and three linear coordinates).

Figure 2A:
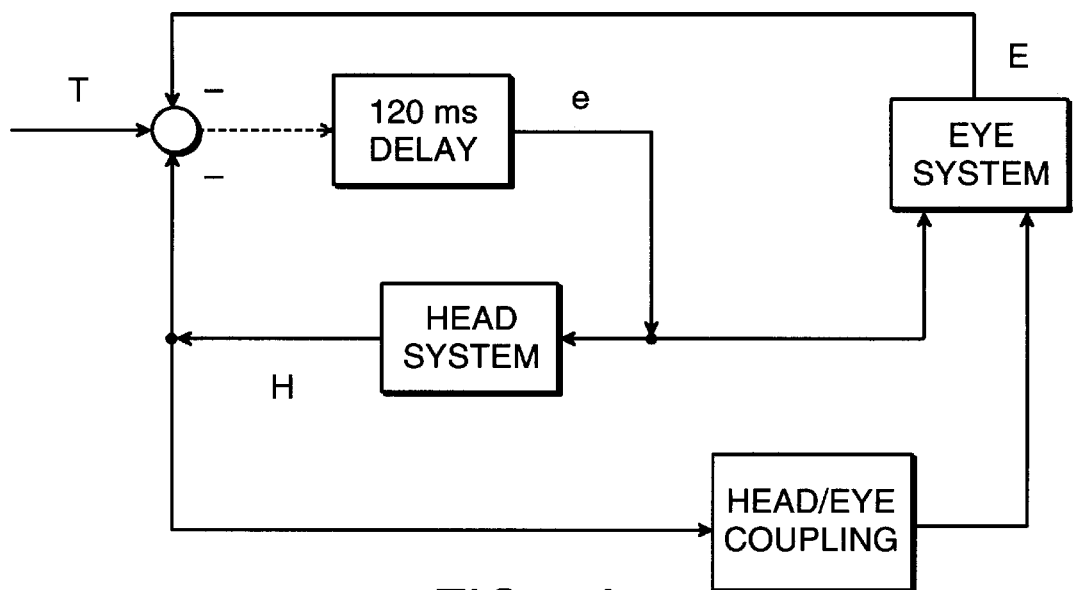
FIG. 2A is a functional block diagram of the apparatus of FIG. 1.
Figure 2B:
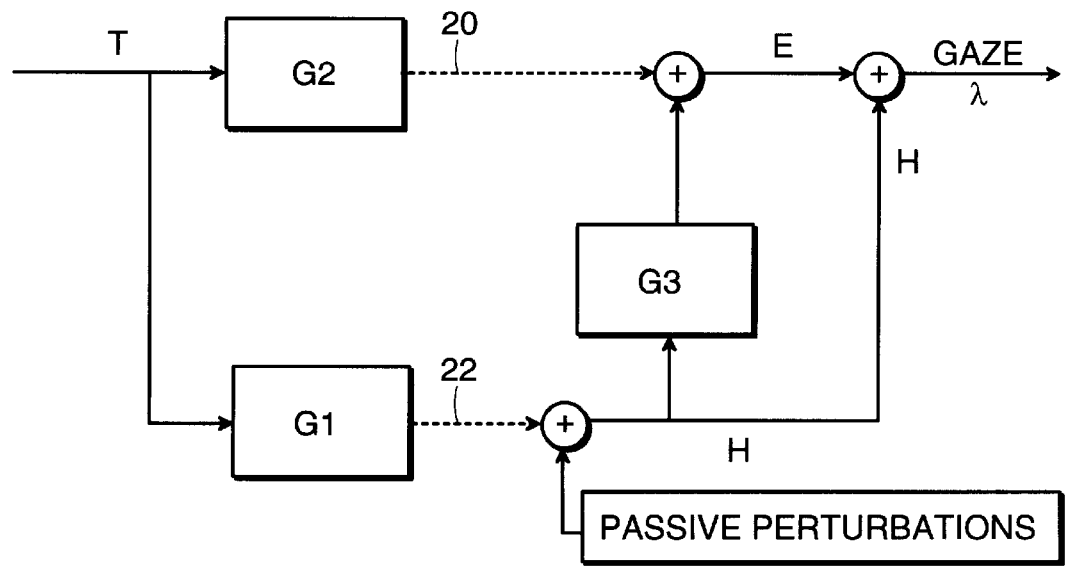
FIG. 2B is a schematic diagram of an equivalent feedforward system to the functional block diagram of FIG. 2A.

In FIGS. 2A and 2B and below, the variables of interest are:
T—the visual target angle in space;
H—head angle on the body;
E—conjugate eye angle relative to the head;
λ—gaze, the angle of the line of sight relative to the body (E+H); and
e—the retinal error (T-λ).

FIG. 2A shows that any head movement will influence eye deviations via the Head/Eye Coupling system (vestibular sensors & processors), usually ascribed to the VOR. In addition, in the presence of visual goals, both eyes and head will respond directly to retinal error, though with different dynamics. FIG. 2B presents an alternate and equivalent view of these processes, with the visual feedback effects now imbedded in transfer functions G1–G3. Passive head perturbations (as may occur in classical rotation tests) are now explicitly shown.

In the dark, the dashed pathways 20 and 22 are presumed open, hence the VOR may be defined by an estimation of G3 during passive whole body or head rotations. This is the basis of classical VOR testing in the dark, despite the fact that cognitively evoked visual goals may interact with the vestibular sensations and bias the estimates. In the light, with active dashed pathways 20 and 22, eye and head trajectories are easily correlated during classical VOR tests. For example, VOR enhancement, T=-H; for target fixed in space;
VOR suppression, T=H; for target fixed with respect to head.

As a result, the estimated VOR (E/H) is a biased estimate of G3, reflecting the contribution of both visual and vestibular mechanisms. Though the true VOR (G3) in the light may be constant, these inappropriate protocols produce the illusion of reported gain changes from 1 to ~0.2. In addition, the visual feedback loops of FIG. 2A are imbedded in the G1–3 transfer functions of FIG. 2B. Hence the estimated dynamics of G3 in the dark need not be the same as those in the dark; this despite placing dashed visual pathways outside G3.

By performing experiments in the light with controlled and uncorrelated stimuli, as taught in the present invention, the corrupting influence of uncontrolled 'mental' targets in the dark and of correlated visual targets may be avoided and optimal and consistent estimation of both visual and vestibular systems may be obtained.

Transfer function G1 represents mapping from visual goals to head trajectories; G2 represents a similar mapping from visual goals to eye trajectories; and G3 represents that process (VOR) causing reflex interactions between eye and head movements. In the exposition below, transfer functions are assumed linear. However, more generally, non-linear techniques are within the scope of the invention and are of particular relevance in the case of lesioned subjects. The analysis below will show that consistent, unbiased, estimates of both VOR and visual tracking dynamics may be obtained with appropriate control over both available stimuli routes.

Natural Eye-Head tracking

In the absence of head perturbations n(t), where n is a function of time, t, natural re-orientation tasks produce correlated eye and head trajectories unsuitable for the estimation of the VOR (G3 transfer function). We have, for pure visual stimuli T(t), the following equations in the Laplace domain:

$$H(s)=G_1(s)T(s),$$

$$E(s)=[G_2(s)+G_1(s)G_3(s)]T(s).$$

In terms of auto or cross-power spectra, $\Phi_{ij}(\omega)$, with subscripts representing input T or outputs E and H, the transfer functions may be estimated from $$G_1(\omega)=\Phi_{HT}(\omega)/\Phi_{TT}(\omega),$$

$$\Psi(\omega)=\{G_2(\omega)+G_1(\omega)G_3(\omega)\}=\Phi_{ET}(\omega)/\Phi_{TT}(\omega).$$

The head-related transfer function is easily extracted. However, VOR ($G_3$) cannot be separated from the overall contributions ($\Psi$) in the ocular responses. Since $\Psi$ is normally estimated in classical VOR testing, this explains its variability with associated visual tasks. An alternative relies on inserting additional head perturbations during natural tasks.

Perturbed Eye-Head tracking

In this case, the head is perturbed externally during reorientation tasks. Hence we now have potentially two controlled and uncorrelated stimuli: the target trajectory in space (T) and external forces on the head perturbing its position (n). In this case $$H(s)=G_1(s)T(s)+n(s),$$

$$E(s)=[G_2(s)+G_1(s)G_3(s)]T(s)+G_3(s)\,n(s).$$

Let $\Psi(\omega)=\{G_2(\omega)+G_1(\omega)G_3(\omega)\}$; then in terms of power spectra again we have, $$\Phi_{HT}(\omega)G_1(\omega)\Phi_{TT}(\omega)+\Phi_{nT}(\omega),$$

$$\Phi_{ET}(\omega)=\Psi(\omega)\Phi_{TT}(\omega)+G_1(\omega)\Phi_{nT}(\omega),$$

$$\Phi_{En}(\omega)=\Psi(\omega)\Phi_{Tn}(\omega)+G_3(\omega)\Phi_{nn}(\omega).$$

If the perturbation is selected optimally so that $\Phi_{nT}(\omega)=0$ (uncorrelated stimuli), then we can identify all the desired transfer functions, namely:

Head tracking performance: $G_1(\omega)=\Phi_{HT}(\omega)/\Phi_{TT}(\omega)$;
Global eye tracking performance: $\Psi(\omega)=\Phi_{ET}(\omega)/\Phi_{TT}(\omega)$;
VOR: $G_3(\omega)=\Phi_{En}(\omega)/\Phi_{nn}(\omega)$;
Gaze tracking: (important behaviorally) $G(\omega)/T(\omega)=G_1(\omega)+\Psi(\omega)$;
Direct visual contribution to eye tracking: $G_2(\omega)=\Psi(\omega)-G_1(\omega)G_3(\omega)$.

A single protocol may thus simultaneously provide consistent estimates of several visual and vestibular reflexes. In cases where absolutely uncorrelated stimuli may not be achieved, a more general solution is available, so long as there is some uncorrelated power available in the frequency range of interest. That is, if the coherence between T and n is less than one, then, (using $\Phi_{nT}=\Phi^*_{Tn}$):

$$\Psi(\omega)=[\Phi_{ET}\Phi_{nn}-\Phi_{nT}\Phi_{En}]/[\Phi_{TT}\Phi_{nn}-|\Phi_{nT}|^2],$$

$$G_3(\omega)=[\Phi_{En}\Phi_{TT}-\Phi_{Tn}\Phi_{ET}]/[\Phi_{TT}\Phi_{nn}-|\Phi_{nT}|^2],$$

$$G_1(\omega)=(\Phi_{HT}-\Phi_{nT})/\Phi_{TT}.$$

In accordance with alternate embodiments of the invention, non-linear identification routines, such as, for example, the iterative solutions applied by Korenberg & Hunter to cascade LNL systems ("The Identification of Non Linear Biological Systems: LNL Cascade Models," in *Biological Cybernetics*, vol. 55, pp. 125–34, 1996) may be applied within the scope of the invention.

Figure 3:
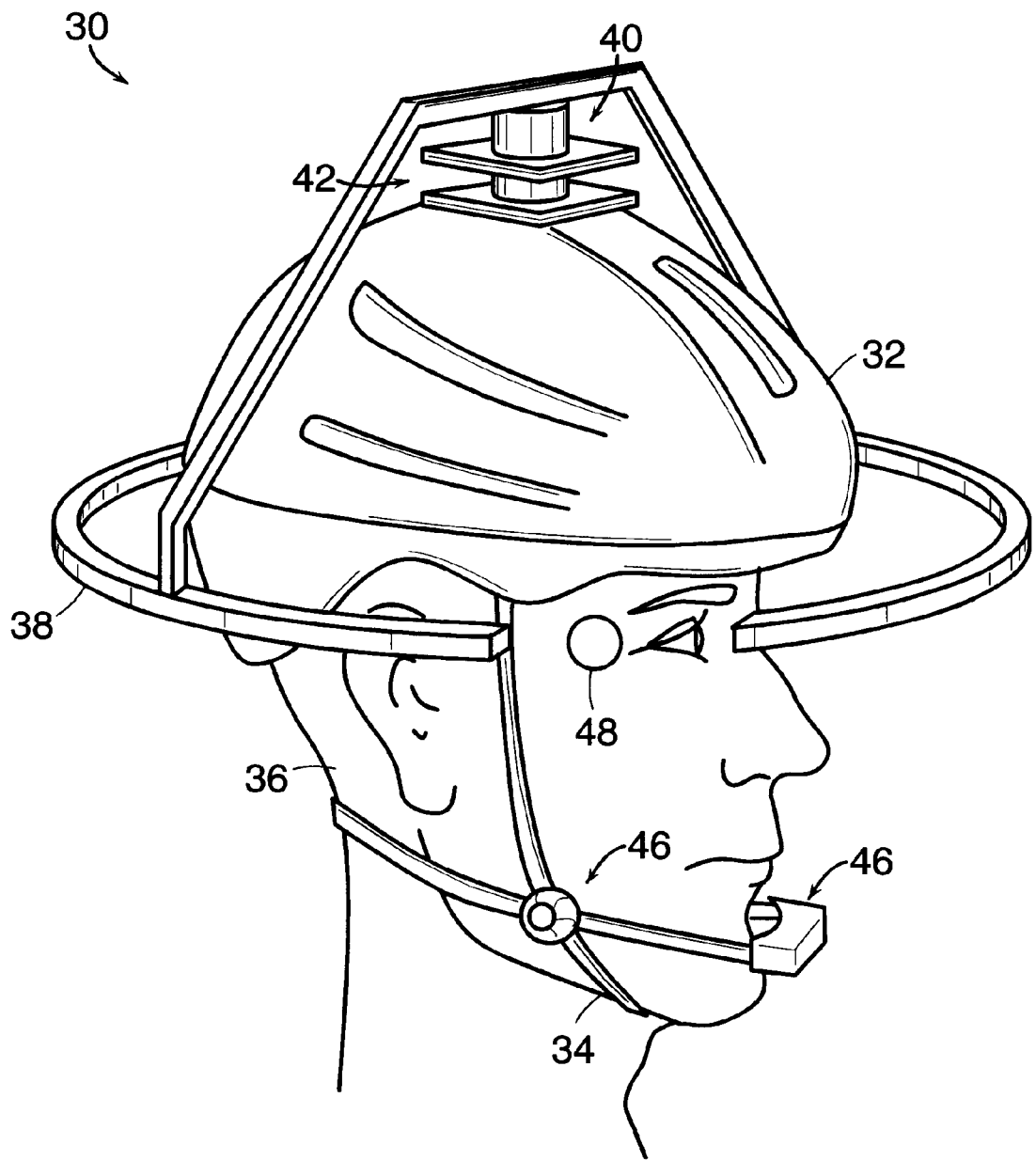
FIG. 3 depicts a helmet applied to the head of a subject for perturbing the head, and sensors for measuring motion of the subject's head and eyeball in accordance with an embodiment of the present invention.

Referring now to FIG. 3, an inertial head perturber, designated generally by numeral 30, is shown for implementing the methods of VOR measurement and analysis which have heretofore been described. Inertial head perturber 30 has a helmet 32, preferably polystyrene, attached with straps 34 to head 36 of the subject, and a ring 38 that surrounds the base of helmet 32. Torque transducer 40 and servomotor 42 are mounted on top of helmet 32. Ring 38 is preferably aluminum, however other materials may be used within the scope of the invention. Low-frequency (typically in the range of 0–40 Hz) torque perturbances of head 36 are applied by oscillating ring 38 in the horizontal plane, with torque typically in the range of less than 1.5 N–m. During testing, subject's head 36 undergoes accelerations typically less than 100 rad s$^{-2}$, and does not attain speeds greater than 20 rad s$^{-1}$. Servomotor 42 may be powered by batteries (not shown) and digitally controlled by a computer. The maximum excursion of head 36 induced by head perturber 30 is preferably on the order of 15 degrees. Rotational velocity sensors 46 and EOG electrodes 48, as described above, are shown.

The apparatus and methods heretofore described may also be used advantageously for rehabilitating a subject suffering from a vestibular deficiency. Once vestibular deficits of the subject are measured, the subject is shown at least one target undergoing slow random motion, and the head of the subject is perturbed with perturbations programmed to stimulate correction of the vestibular deficits of the subject.

Figure 4:
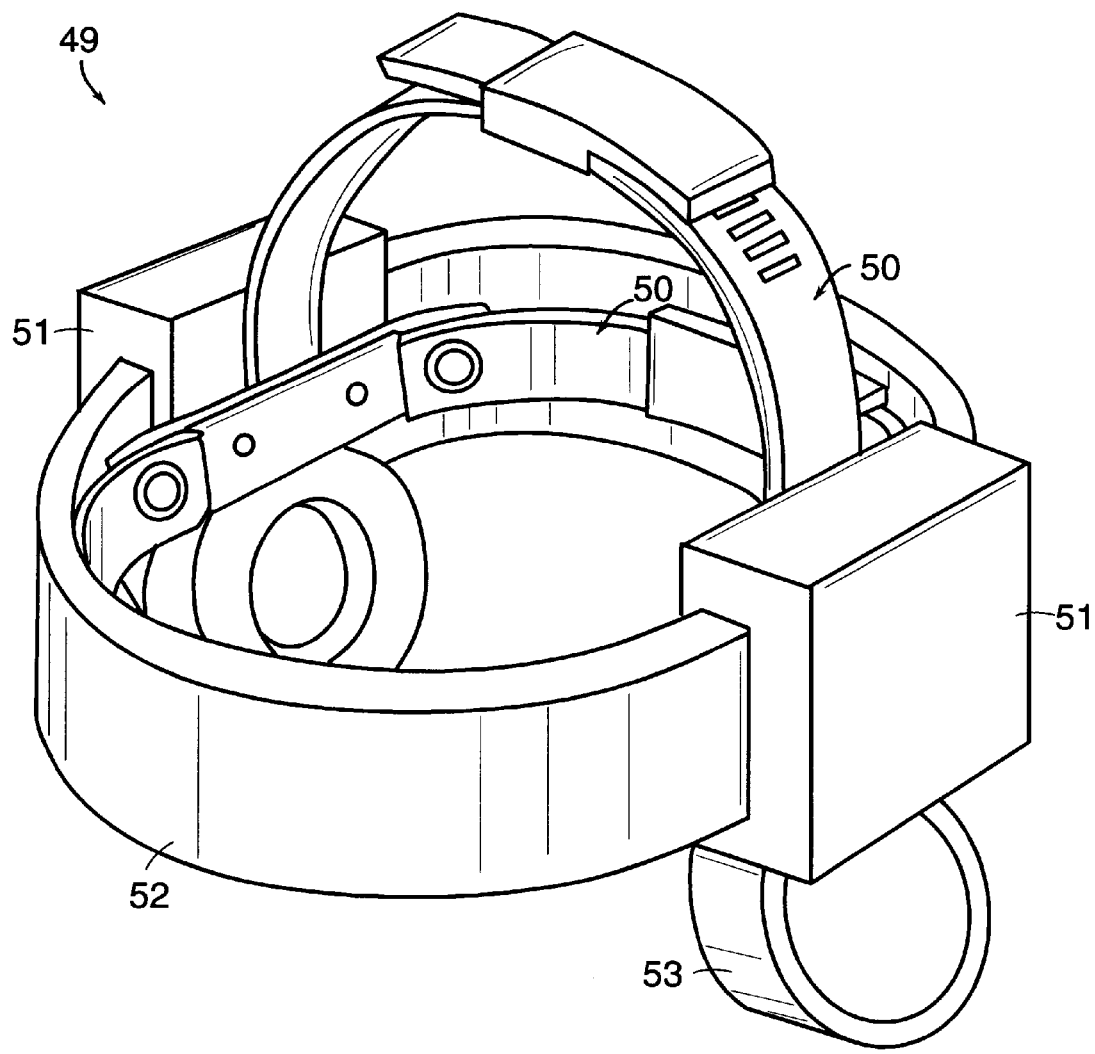
FIG. 4 depicts a headphone-based head attachment device with a Lorentz force liquid metal perturbation mechanism in accordance with an embodiment of the present invention.

Referring now to FIG. 4, a Lorentz force perturber, designated generally by numeral 49, is shown for implementing the methods of VOR measurement and analysis which have been described above. Lorentz force head perturber 49 has an adjustable head band 50 that attaches to the head of the subject. Lorentz force actuators 51 accelerate a metal ring (not shown) that is free to move within a housing 52. The metal ring is preferably a liquid metal at room temperature, however solid metal may be used within the scope of the invention. Headphones 53 may be used to produce a three-dimensional acoustic target which may supplement or replace the visual target which has heretofore been described.

The described embodiments of the invention are intended to be merely exemplary and numerous variations and modifications will be apparent to those skilled in the art. All such variations and modifications are intended to be within the scope of the present invention as defined in the appended claims.

We claim:

1. A method for analyzing visual and vestibular responses of a subject having a head and at least one eyeball, the method comprising:
   a. displaying to the subject at least one target undergoing slow random motion;
   b. perturbing the head of the subject with perturbations statistically uncorrelated with the random motion of the at least one target;
   c. measuring the response of at least one of the motion of the head of the subject and the motion of the at least one eyeball of the subject; and
   d. estimating visual and vestibular system response dynamics based on the measured response.

2. A method according to claim 1, wherein the step of displaying includes visually displaying a target.

3. A method according to claim 1, wherein the step of displaying includes auditorially displaying a target.

4. A method according to claim 1, further comprising:
   a. comparing the measured response of the subject with accumulated data in such a manner as to distinguish a functionally normal subject from a functionally deficient subject.

5. A method for analyzing the interaction between vergence, head processing, and conjugate eye reflexes in a subject having a head and two eyeballs, the method comprising:
   a. displaying to the subject at least one target undergoing slow random motion;

b. perturbing the head of the subject with perturbations statistically uncorrelated with the random motion of the at least one target;

c. measuring the response of the motion of the head of the subject and the motion of the eyeballs of the subject; and d. estimating visual and vestibular system coupling based on the measured response.

6. A method for classifying the qualification for a specified function of an individual having a head and at least one eyeball, the method comprising:

a. displaying to the individual at least one target undergoing slow random motion;

b. perturbing the head of the individual with perturbations statistically uncorrelated with the random motion of the at least one target;

c. measuring the response of at least one of the motion of the head of the individual and the motion of the at least one eyeball;

d. estimating visual and vestibular system response dynamics based on the measured response; and e. comparing the measured response of the individual with predetermined ranges of acceptable responses in such a manner as to distinguish a capable candidate from a deficient candidate.

7. A method for rehabilitating a subject suffering from a vestibular deficiency, the method comprising:

a. determining the vestibular deficits of the subject;

b. displaying to the subject at least one target undergoing slow random motion;

c. perturbing the head of the subject with perturbations programmed to stimulate correction of the vestibular deficits of the subject.

8. A portable apparatus for analyzing visual and vestibular responses of a subject having a head and at least one eyeball, the apparatus comprising:

a. a perturber for applying a torque perturbation to the head of the subject;

b. a transducer for measuring the torque applied to the head of the subject;

c. a head position tracker for measuring rotational movement of the head of the subject;

d. an eye tracker for measuring the motion of the at least one eyeball of the subject; and e. a controller for estimating visual and vestibular system response dynamics based on the measured rotational movement of the head of the subject and motion of the at least one eyeball of the subject.

9. An apparatus according to claim 8, further comprising a transducer for measuring the torque applied to the head of the subject.

10. An apparatus according to claim 8, wherein the perturber includes a water jet.

11. An apparatus according to claim 8, further including a helmet disposed upon the head of the subject for transmitting torque perturbations applied by the perturber.

12. An apparatus according to claim 11, wherein the perturber comprises a servomotor for applying a torque to the helmet with respect to a reaction ring disposed circumferentially about the helmet.

13. An apparatus according to claim 8, wherein the head position tracker is a rotational velocity sensor.

14. An apparatus according to claim 8, wherein the eye tracker is an electro-oculograph.

15. An apparatus according to claim 8, wherein the eye tracker is a corneal reflection eye tracker.

16. An apparatus according to claim 8, wherein the perturber is disposed upon a flexible band for retaining the perturber in contact with the head of the subject.

17. An apparatus according to claim 8, wherein the controller includes a memory storage containing accumulated data such that the measured response of the subject is compared with accumulated data so as to distinguish a functionally normal subject from a functionally deficient subject.

18. An apparatus according to claim 8, further including a visual target for directing the motion of the at least one eyeball of the subject.

19. An apparatus according to claim 8, further including a three-dimensional acoustic target for directing the motion of the at least one eyeball of the subject.

20. An apparatus according to claim 8, further including a headphone device for transmitting torque perturbations applied by the perturber to the head of the subject.

21. An apparatus according to claim 8, wherein the perturber includes a Lorentz force actuator for accelerating a metal ring disposed circumferentially about the helmet in such a manner as to apply torque to the head of the subject.

22. An apparatus for rehabilitating a subject suffering from a vestibular deficiency, the apparatus comprising:

a. a perturber for applying a torque perturbation to the head of the subject;

b. a transducer for measuring the torque applied to the head of the subject;

c. a head position tracker for measuring rotational movement of the head of the subject;

d. an eye tracker for measuring the motion of the at least one eyeball of the subject; and e. a controller for driving the perturber with signals programmed to stimulate correction of the vestibular deficits of the subject.

\* \* \* \* \*